United States Patent [19]

Hill

[11] Patent Number: 4,490,383

[45] Date of Patent: Dec. 25, 1984

[54] PHARMACEUTICAL COMPOSITION

[75] Inventor: Stuart A. Hill, Worthing, England

[73] Assignee: Beecham Group Limited, England

[21] Appl. No.: 448,240

[22] Filed: Dec. 9, 1982

Related U.S. Application Data

[60] Continuation of Ser. No. 57,942, Jul. 16, 1979, abandoned, which is a continuation of Ser. No. 792,723, May 2, 1977, abandoned, which is a continuation of Ser. No. 133,869, Mar. 25, 1980, abandoned, which is a continuation of Ser. No. 954,420, Oct. 25, 1978, abandoned, which is a division of Ser. No. 792,723.

[30] Foreign Application Priority Data

May 13, 1976 [GB] United Kingdom ............... 19652/76

[51] Int. Cl.$^3$ .............................................. A61K 31/43

[52] U.S. Cl. ..................................................... 424/271
[58] Field of Search ........................................ 424/271

[56] References Cited

U.S. PATENT DOCUMENTS 4,029,804  6/1977  Clark ................................... 424/271

Primary Examiner—Stanley J. Friedman
Attorney, Agent, or Firm—Jacobs & Jacobs

[57] ABSTRACT

A pharmaceutical composition adapted for administration to a human by injection which composition comprises an aqueous solution containing sodium amoxycillin and tri-sodium phosphate, the weight ratio of sodium amoxycillin present to the tri-sodium phosphate present being from 8:1 to 50:1.

26 Claims, No Drawings

PHARMACEUTICAL COMPOSITION

CROSS-REFERENCE

This is a continuation of Ser. No. 057,942 filed July 16, 1979 which is a continuation of Ser. No. 792,723 filed May 2, 1977 now abandoned which is a continuation of Ser. No. 133,869 filed Mar. 25, 1980 which is a continuation of Ser. No. 954,420 filed Oct. 25, 1978 now abandoned which is itself a divisional of Ser. No. 792,723 filed May 2, 1977 now abandoned.

The present invention relates to injectable pharmaceutical compositions containing sodium amoxycillin.

British Patent Specification No. 1,241,844 discloses inter alia amoxycillin and salts thereof. Amoxycillin which is the penicillin of the formula (I):

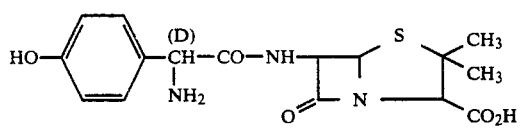

is widely recognised as having broad spectrum antibacterial activity of a high order. One of amoxycillin's great advantages is that it is very well absorbed after oral administration but there are occasions when it is desirable to administer it parenterally. It is possible to use the methods disclosed in British Patent Specification No. 1,241,844 to form the sodium salt of amoxycillin which may then be dissolved in sterile water and used as an injectable composition. However, these previously known sodium salts tend to be incompletely soluble in water at some of the concentrations necessary for parenteral use. Clearly this disadvantage does not prevent use of the known sodium salts in forming injectable compositions of amoxycillin but it would be more convenient for medical practitioners if there was available an injectable amoxycillin preparation that was completely dissolvable. Such a composition has now been discovered.

Accordingly, the present invention provides a pharmaceutical composition adapted for administration to a human by injection, which composition comprises sodium amoxycillin and tri-sodium phosphate, the weight ratio of the sodium amoxycillin to the tri-sodium phosphate being from 8:1 to 50:1.

When used herein the term 'injection' includes 'infusion' so that it should be realised that the compositions of this invention are suitable for administration by intravenous injection or infusion as well as intra-muscular injection.

One particularly useful aspect of the invention provides a pharmaceutical composition adapted for administration to a human by injection which composition comprises an aqueous solution containing sodium amoxycillin and tri-sodium phosphate, the weight ratio of sodium amoxycillin present to the tri-sodium phosphate present being from 8:1 to 50:1.

When used herein the term 'aqueous solvent' means water or water mixed with one or more pharmaceutically acceptable alcoholic compounds such as ethanol, n-propanol, iso-propanol, diethylene glycol, propylene glycol or glyceraldehyde. Normally not more than two and usually not more than one such alcoholic compound will be included in the solvent.

Particularly suitable aqueous solvents include water and water mixed with up to 30% (by volume) of ethanol or propylene glycol.

The preferred aqueous solvent for use in compositions of this invention is water.

The solutions of the invention have useful stability.

From an alternative viewpoint the present invention provides a solid pharmaceutical composition which may be dissolved in an aqueous solvent and used for injection which composition comprises sodium amoxycillin and tri-sodium phosphate, the weight ratio of sodium amoxycillin to tri-sodium phosphate being from 8:1 to 50:1. Such compositions are of particular advantage due to their ease of preparation and use.

From a further aspect the present invention provides a pharmaceutical composition in the form of a two-pack container or two-part syringe wherein one pack or part contains a quantity of sodium amoxycillin in the form of a dry powder and the second pack or part contains an aqueous solution of tri-sodium phosphate, the weight ratio of sodium amoxycillin to tri-sodium phosphate being from 8:1 to 50:1.

From another aspect the present invention provides a pharmaceutical composition in the form of two-pack container or two-part syringe wherein one pack or part contains sodium amoxycillin in the form of a dry powder together with tri-sodium phosphate in the form of a dry solid, the weight ratio of a sodium amoxycillin to tri-sodium phosphate being from 8:1 to 50:1, and the second pack or part contains an aqueous solvent.

From yet another aspect, the present invention provides a pharmaceutical composition in the form of a two-pack container wherein one pack contains sodium amoxycillin and the other pack contains tri-sodium phosphate, the weight ratio of sodium amoxycillin to tri-sodium phosphate being from 8:1 to 50:1.

For all aspects of this invention the ratio of sodium amoxycillin to tri-sodium phosphate present is more suitably from 10:1 to 30:1 and is preferably from about 14:1 to about 28:1, for example about 28:1.

Normally the compositions of this invention are administered in the form of 5–30% solutions (based on the weight of sodium amoxycillin present). Thus the amount of aqueous solvent present in the second part or pack of the aforementioned two-part compositions is sufficient to form a 5–30% solution.

Preferably the compositions of this invention are presented in unit dose form which normally contain the equivalent of about 125 mg, 250 mg, 375 mg, 500 mg, 750 mg, 1 g, 2 g, 4 g, or 5 g of pure amoxycillin free acid. In accordance with conventional practice these unit-dosage forms will usually contain about 5–10% more sodium amoxycillin than the nominal quantity to permit easy withdrawal of the required dose and to allow for decomposition on long storage.

Normally the compositions of this invention will be contained in glass or plastic bottles or ampoules or their equivalents.

The various aspects of this invention may, if desired, also comprise conventional excipients used in injectable compositions such as salts to render the final injectable solutions isotonic with the blood.

All injectable components of this invention should be rendered sterile. This may be achieved in any convenient manner such as by heating, irradiation or sterile filtering.

The tri-sodium phosphate used for preparing the compositions of this invention may be hydrated, for example the dodecahydrate, or may be non-hydrated. It is frequently preferable to use dried material, for example containing not more than 3% water and preferably not more than 2% water (by Karl-Fischer analysis) as use of such dried material in the preparation of dry compositions of this invention can lead to compositions having particularly good storage characteristics.

The trisodium phosphate may be prepared suitably dry and sterile by dissolving in pyrogen-free distilled water, and passing the solution through a sterilising filter into sterile methanol. The precipitated tri-sodium phosphate is filtered off and dried in a hot air oven under aseptic conditions. Alternatively, and preferably, the sterile aqueous solution is dried by spray drying in an aseptic spray-drying system, such as that described by Masters and Vestergaard in 'Aseptic and Closed Cycle Spray Drying in Pharmaceuticals/Bio-chemicals Manufacture', Process Biochemistry, January/February 1975, page 21.

Sodium amoxycillin for use in the compositions of this invention may be prepared by such conventional methods as those disclosed in British Patent Specification No. 1,241,844.

The invention also provides a process for preparing the compositions of the invention, which process comprises bringing into association the sodium amoxycillin and the tri-sodium phosphate.

The exact nature of this process of course varies with the nature of the composition to be prepared.

The compositions of the invention in the form of aqueous solutions maybe prepared by dissolving the sodium amoxycillin and the tri-sodium phosphate in an aqueous solvent. This process maybe carried out by: (a) dissolving solid sodium amoxycillin in a solution of tri-sodium phosphate in an aqueous solvent or by (b) dissolving a dry mixture of solid tri-sodium phosphate and solid sodium amoxycillin in an aqueous solvent or by (c) dissolving solid tri-sodium phosphate in a solution of sodium amoxycillin in an aqueous solvent or by (d) mixing a solution of tri-sodium phosphate in an aqueous solvent with a solution of sodium amoxycillin in an aqueous solvent.

The 'solid' pharmaceutical compositions of the invention maybe prepared by mixing together the sodium amoxycillin and the tri-sodium phosphate.

The pharmaceutical compositions in the form of two-pack containers or two-part syringes maybe prepared by filling the appropriate ingredients into the appropriate packs or parts.

The invention also provides a method of treatment of disease in a human, which method comprises the administration by injection of an aqueous solution according to the invention.

The invention further provides a method of improving the solubility of sodium amoxycillin in an aqueous solvent, which method comprises adding to the solvent sufficient tri-sodium phosphate to provide a weight ratio between the sodium amoxycillin and tri-sodium phosphate of from 8:1 to 50:1.

Suitably this method is carried out by preparing compositions in the form of aqueous solutions in the manner of the invention as hereinbefore described.

The following Examples illustrate the invention:

EXAMPLE 1

1 kg. of trisodium phosphate dodecahydrate, of a purity suitable for injection into humans, was dissolved in 3.5 liters of pyrogen—free distilled water and filtered through a 0.22$\mu$ cellulose acetate filter into excess methanol. The precipitated phosphate was filtered off using a sintered glass filter and dried in a hot air oven, and finally sterilised by heating for 1 hour at 160° C. All further processing was carried out aseptically under conditions of relative humidity not exceeding 40%. After cooling, the phosphate was milled in a hammer mill at fast speed with hammers forward using a 0.040 inch screen.

3 kg. of sterile sodium amoxycillin was hammer-milled separately at fast speed with hammers forward using a 0.125 inch screen. A weight of the milled sodium amoxycillin equivalent to 1 kg. of amoxycillin was placed in a sterile blender and 50 g. of the sterile milled trisodium phosphate added. The powders were blended until uniformly mixed, transferred to sterile filling equipment, and filled into clean sterile vials at a filling weight equivalent to 538 mg. of amoxycillin per vial.

EXAMPLE 2

Vials for injection were prepared exactly as described in Example 1, but using 100 g. of trisodium phosphate.

EXAMPLE 3

A solution of trisodium phosphate dodecahydrate, in Water for Injections B.P. was prepared, at a strength equivalent to 1.08% w/v of anhydrous salt. The solution was sterilised by filtration and filled into ampoules of alkali-resistant glass at 2.8 ml. per ampoule. Sterile sodium amoxycillin was filled into vials at a weight equivalent to 538 mg. of amoxycillin per vial. An injectable composition was prepared by adding 2.5 ml. of the phosphate solution to the contents of one vial of sodium amoxycillin and shaking until dissolved.

EXAMPLE 4

The compositions as described in Example 3 were prepared, using trisodium phosphate at a strength equivalent to 2.16% w/v of anhydrous salt.

EXAMPLE 5

A mixture of absolute ethanol 1 part by volume and Water for Injections B.P. 3 parts was made, sterile-filtered, and filled into ampoules at 2.8 ml. per ampoule. An injectable composition was prepared by adding 2.5 ml. of the mixture to one vial of the composition described in Example 1.

EXAMPLE 6

An injectable composition was prepared as described in Example 5, using a vehicle consisting of 1 part by volume of propylene glycol, 3 parts Water for Injections B.P.

EXAMPLE 7

A composition as described in Example 3 was prepared, using a solution of the trisodium phosphate in the mixture of ethanol and Water for Injections of Example 5.

EXAMPLE 8

A composition as described in Example 3 was prepared, using a solution of the trisodium phosphate in the mixture of propylene glycol and Water for Injections of Example 6.

EXAMPLE 9

1 kg. of trisodium phosphate dodecahydrate was dissolved in 3.5 liters of pyrogen-free distilled water and the solution sterile-filtered through a 0.22μ cellulose acetate filter. The solution was spray-dried under aseptic conditions at a rate of 2 liters per hour with an inlet temperature of 200°–210° C., and outlet temperature of 100°–102° C.

The sterile spray-dried sodium phosphate was blended with sterile sodium amoxycillin in the same amounts and in the same manner as described in Example 1.

EXAMPLE 10

Vials for injection were prepared exactly as described in Example 9, but using 100 g. of trisodium phosphate.

What we claim is:

1. A pharmaceutical composition adapted for administration to a human by injection, which composition comprises sodium amoxycillin and tri-sodium phosphate, the weight ratio of the sodium amoxycillin to the trisodium phosphate being from 8:1 to 50:1.

2. A pharmaceutical pack for formulation of an injectable sterile aqueous solution of the sodium salt of amoxycillin and trisodium phosphate in an aqueous solvent in a weight ratio of sodium salt of amoxycillin to trisodium phosphate of from 8:1 to 50:1, said pack comprising as a first component an antibacterially therapeutic amount of sodium amoxycillin in the form of a sterile dry powder, as a second component a sterile solution of trisodium phosphate in an aqueous solvent, said trisodium phosphate being present in said solution in an amount of from ⅛th to 1/50th by weight of the amount of said sodium amoxycillin with said solvent being present in an amount sufficient upon mixing with said sodium amoxycillin to produce a concentration of sodium amoxycillin of from 5 to 30% by weight, and means operable to prevent premature mixing of said first and second components.

3. A pharmaceutical pack according to claim 2 which is a two part-syringe.

4. A pharmaceutical pack according to claim 2 wherein said aqueous solvent consists of water.

5. A pharmaceutical pack according to claim 2 wherein said aqueous solvent contains up to 30% by volume of ethanol.

6. A pharmaceutical pack according to claim 2 wherein said aqueous solvent contains up to 30% by volume of propylene glycol.

7. A pharmaceutical pack for formulation of an injectable sterile aqueous solution of the sodium salt of amoxycillin and trisodium phosphate in an aqueous solvent in a weight ratio of sodium salt of amoxycillin to trisodium phosphate of from 8:1 to 50:1, said pack comprising as a first component an intimate mixture of an antibacterially therapeutic amount of sodium amoxycillin in the form of a sterile dry powder and trisodium phosphate as a sterile dry powder in an amount of from ⅛th to 1/50th by weight of the amount of said sodium amoxycillin, as a second component an aqueous solvent, said solvent being present in an amount sufficient upon mixing with said sodium amoxycillin to produce a concentration of sodium amoxycillin of from 5 to 30% by weight, and means operable to prevent premature mixing of said first and second components.

8. A pharmaceutical pack according to claim 2 which is a two-part syringe.

9. A pharmaceutical pack according to claim 2 wherein said aqueous solvent consists of water.

10. A pharmaceutical pack according to claim 2 wherein said aqueous solvent contains up to 30% by volume of ethanol.

11. A pharmaceutical pack according to claim 2 wherein said aqueous solvent contains up to 30% by volume of propylene glycol.

12. A pharmaceutical pack according to claim 2 wherein said trisodium phosphate is trisodium phosphate dodecahydrate.

13. A pharmaceutical pack for formulation of an injectable sterile aqueous solution of the sodium salt of amoxycillin and trisodium phosphate in an aqueous solvent in a weight ratio of sodium salt of amoxycillin to trisodium phosphate of from 8:1 to 50:1, said pack comprising as a first component an antibacterially therapeutic amount of sodium amoxycillin in the form of a sterile dry powder, as a second component a sterile solution of trisodium phosphate in an aqueous solvent, said trisodium phosphate being present in said solution in an amount of from ⅛th to 1/50th by weight of the amount of said sodium amoxycillin with said solvent being present in an amount sufficient upon mixing with said sodium amoxycillin to produce a concentration of sodium amoxycillin of from 5 to 30% by weight, and means operable to prevent premature mixing of said first and second components.

14. A solid composition for preparation of an injectable aqueous solution comprising an intimate physical mixture of the sodium salt of amoxycillin and trisodium phosphate in a weight ratio of from 8:1 to 50:1.

15. A solid composition according to claim 14 wherein the weight ratio of the sodium salt of amoxycillin to trisodium phosphate is from 10:1 to 30:1.

16. A solid composition according to claim 14 wherein the weight ratio of the sodium salt of amoxycillin to trisodium phosphate is from 14:1 to 28:1.

17. A solid composition according to claim 14 wherein said trisodium phosphate is trisodium phosphate dodecahydrate.

18. A solid composition according to claim 14 wherein said trisodium phosphate is spray dried trisodium phosphate.

19. An injectable pharmaceutical composition comprising a sterile aqueous solution of (a) an antibacterially therapeutic amount of the sodium salt of amoxycillin and (b) tri-sodium phosphate in an aqueous solvent, the weight ratio of the sodium salt of amoxycillin to trisodium phosphate being from 8:1 to 50:1.

20. An injectable pharmaceutical composition according to claim 19 wherein the weight ratio of the sodium salt of amoxycillin to trisodium phosphate from 10:1 to 30:1.

21. An injectable pharmaceutical composition according to claim 19 wherein the weight ratio of the sodium salt of amoxycillin to trisodium phosphate is from 14:1 to 28:1.

22. An injectable pharmaceutical composition according to claim 19 wherein the concentration of said sodium salt of amoxycillin is from 5% to 30% by weight of said salt.

23. An injectable pharmaceutical composition according to claim 19 wherein said aqueous solvent contains up to 30% by volume of ethanol.

24. An injectable pharmaceutical composition according to claim 19 wherein said aqueous solvent contains up to 30% by volume of propylene glycol.

25. An injectable pharmaceutical composition according to claim 19 wherein said aqueous solvent consists of water.

26. In an injectable pharmaceutical solution of sodium amoxycillin the improvement which comprises the presence in said solution of trisodium phosphate in a weight ratio of sodium amoxycillin to trisodium phosphate of from 8:1 to 50:1.

* * * * *